United States Patent [19]
Lyttle

[11] Patent Number: 5,877,284
[45] Date of Patent: Mar. 2, 1999

[54] ISOLATED CHEMOTACTIC FACTOR FROM PATIENTS WITH ENDOMETRIOSIS

[75] Inventor: C. Richard Lyttle, Bala Cynwyd, Pa.

[73] Assignee: The Trustees of the University of Pennsylvania, Philadelphia, Pa.

[21] Appl. No.: 460,326

[22] Filed: Jun. 2, 1995

Related U.S. Application Data

[63] Continuation of Ser. No. 195,693, Feb. 16, 1994, abandoned.

[30] Foreign Application Priority Data

Aug. 12, 1993 [JP] Japan .................................. 5-219255
Aug. 16, 1993 [AU] Australia ............................... 44675/93

[51] Int. Cl.$^6$ ......................... C07K 14/435; C07K 14/52
[52] U.S. Cl. ......................... 530/351; 530/300; 530/350; 530/395; 530/412
[58] Field of Search .................................. 530/300, 350, 530/351, 412, 395

[56] References Cited

FOREIGN PATENT DOCUMENTS 2-138200  5/1990  Japan .

OTHER PUBLICATIONS

Leiva et al. Am J. Obstet Gynecol 168: 592–598(1993).
Mori et al. Am J Reprod Immunol 26: 62–67(1991).
Eisermann et al. Fertil Steril 50: 573–579(1988).
Tabibzadeh Endocrine Reviews 12: 272–290 (1991).
Badawy S. Z., et al., Cellular components in peritoneal fluid in infertile patients with and without endometriosis *Fertil Steril* 1984 42:704.
Buttram et al. Treatment of endometrosis with Danazol *Fertil Steril* 1985 43:353.
Fakih et al., Interleukin–1: a possible role in the infertility associated with endometriosis *Fertil Steril* 1987 47:213.
American Fertility Society Revised American Fertility Society Classification of Endometriosis *Fertil Steril* 1985 43:351.
Halme J. et al., Increased activation of pelvic macrophages in infertile women with mild endometriosis *Am J Obstet Gynecol* 1983 145:133.
Halme J. et al., Peritoneal Macrophages From Patients With Endometriosis Release Growth Factor Activity in Vitro *J. Clin Endocrinol Metal* 1988 66:1044.
Halme J. et al., Release of Tumor Necrosis Factor–α by Human Peritoneal macrophages in vivo and invitro *Am J. Obstet Gynecol* 1989 161:1718.

Haney A. F., et al Reduction of the intraperitoneal inflammation associated with endometriosis by treatment with medroxyprogesterone acetate *Am J. Obstet Gynecol* 1988 159:450.
Leiva et al., Increased Chemotactic Activity of Peritoneal Fluid in Patients with Mild to Moderate Endometriosis *Am Fertil Soc.* 47th. Annual Meeting, Oct. 19–24, 1991.
Howe R.S., et al., Chemotactic Capabilities of HL–60 Human Myeloid Leukemia Cells Differentiated to Eosinophils *Exp Hematol* 1990 18:299.
Howe et al. Glucocorticoid and Progestin Regulation of Eosinophil Chemotactic Factor and Complement C3 in the Estrogen–Treated Rat Uterus *Endocrinology* 1990 126:3193.
Hill, J A et al., Lymphocyte activity in the presence of peritoneal fluid from fertile women and infertile women with and without endometriosis *Am J. OBstet Gynecol* 1989 161:861.
Kay G.E., et al Induction of Selective Biological Responses to Chemoattractants in a Human Monocyte–Like Cell Line *Infect Immun* 1983 41:1166.
Kohler and Milstein, Continuous Cultures of Fused Cells secreting antibody of predefined specificity *Nature* 1975 256:495.
Lee Y.H., et al Estrogen Regulation of an Eosinophil Chemotactic Factor in the Immature Rat Uterus *Endocrinology* 1989 125:3022.
Leiva M. et al, Increased chemotactic activity of peritoneal fluid in patients with endometriosis *Am J. Obstet and Gynecol* 1993 168:592.
Sundstromm C et al. Establishment and Characterization of a Human Histiocytic Lymphona Cell Line *Int J. Cancer* 1976 17:565.
Mori et al., Am. J. Reprod. Immunol. 1993, 168:592–598.
Tabibzadeh, Endocrine Reviews, 1991, 12:272–290.
Eiserman et al, Fertil. Steil. 1988, 50:573–579.

*Primary Examiner*—Christina Y. Chan
*Assistant Examiner*—Phillip Gambel
*Attorney, Agent, or Firm*—Woodcock Washburn Kurtz Mackiewicz & Norris, LLP

[57] ABSTRACT

A composition comprising a soluble peptide of about 23 kD to about 29 kD, capable of causing neutrophil and macrophage chemotaxis, and which is substantially similar to chemotactic factor from peritoneal fluid of mammals with minimal or moderate endometriosis.

3 Claims, 13 Drawing Sheets

ISOLATED CHEMOTACTIC FACTOR FROM PATIENTS WITH ENDOMETRIOSIS

This is a continuation of application Ser. No. 08/195,693, filed Feb. 16, 1994, now abandoned.

REFERENCE TO GOVERNMENT GRANTS

This work was supported in part by research grants from the National Institutes of Health, grant numbers HD-20025, HD-06274 and HD-30475. The United States Government may have certain rights in this invention.

BACKGROUND OF THE INVENTION

The underlying mechanisms indicating an association between minimal to moderate endometriosis and infertility are not clearly understood. Recent investigations have focused on the presence of an aseptic inflammation of the peritoneal cavity, resulting in a distortion of the normal function of the pelvic organs, as an important contributory mechanism. Other proposed causes for reproductive failure in the less severe cases of endometriosis include oligoanovulation, luteal phase defects, and luteinized unruptured follicle syndrome. However, these suggestions need to be clearly substantiated and each one cannot be considered the sole cause of infertility in patients with endometriosis. Other factors, which include alterations in the sperm-egg interaction with possible phagocytosis of the sperm or interference with early embryo development, may be taken into consideration when studying the associated infertility of these patients. The biochemical modifications that have been described in endometriosis include an increase in the concentration of prostaglandins, cytokines and complement components in the peritoneal fluid and activation of resident macrophages. Halme J, et al., Am J Obstet Gynecol 1983 145:333 and Hill J A, et al., Am J Obstet Gynecol 1989 161:861. The activation of leukocytes within the peritoneal cavity is evidenced by cytoskeletal rearrangement of the cells and by changes in the lipid metabolism with activation of protein kinases or release of lysosomal enzymes.

The role of peritoneal fluid in the physiologic modifications of the peritoneal cavity of patients who otherwise would seem to have a normal pelvic environment has been studied. Endometriosis without severe anatomic distortion is associated with an increase in the peritoneal fluid volume, cell number, and concentration of lysosomic enzymes as compared with normal fertile controls. The peritoneal fluid arises primarily from two different sources: the plasma as a transudate and the ovary as an exudate; other sources are tubal fluid; retrograde menstruation, and secretions from the macrophages in the cavity. However, the exact source for the biochemical modifications observed in endometriosis is not clear.

Normally the peritoneal fluid contains several types of blood cells, with macrophages and lymphocytes being the most abundant; desquamated endometrial and mesothelial cells are also present. This cellular composition is modified in patients with endometriosis. Badaway S. Z., et al., Fertil Steril 1984 42:704. Several theories exist regarding the mechanisms responsible for these alterations, one of which is considered by the present invention—the presence of a chemotactic stimulus that would attract more cells into the peritoneal cavity, or alternatively, activate and induce proliferation of resident macrophages in response to these unknown factors.

Therefore to study the modifications seen within the pelvic cavity in endometriosis investigators have focused on the initial stages of the disease in which active endometrial glands and stroma are present and are clearly associated with changes in the peritoneal fluid. Some of the modifications include an increase in the concentrations of cytokines and the production of various growth factors by the infiltrating leukocytes. The contribution of these factors to the inflammatory changes of the peritoneal fluid is yet to be determined. Fakih H, et al., Fertil Steril 1987 47:213 and Halme J, et al., J Clin Endocrinol Metab 1988 66:1044.

The role of the peritoneal fluid of patients with minimal to moderate endometriosis was examined in the present invention as a contributor to the inflammatory changes observed in the pelvic cavity of these patients. Leiva, M., et al., Am J Obstet and Gynecol 1993 168:592. In this regard, the chemotactic potential of peritoneal fluid obtained from patients with minimal to moderate endometriosis was investigated. Responsive cells included neutrophils isolated from peripheral blood or HL60-C15-differentiated neutrophils and macrophages derived from U937 cells. These findings were compared with the activity observed in normal patients or patients undergoing medical treatment for this condition.

These results determine the potential of the invention to satisfy the great needs in the art of diagnosis and treatment of endometriosis. Accurate and early methods of detection of endometriosis are needed such that methods of treatment may begin promptly.

SUMMARY OF THE INVENTION

The present invention is directed to a composition comprising a soluble peptide of about 23 kD to about 29 kD. The soluble peptide size is determined by separation on a G-75 SEPHADEX® column followed by G-25 SEPHADEX®/Blue SEPHAROSE® column, a second G-75 SEPHADEX® column, a Anti Ig column and HPLC purification. An alternative purification scheme resulting in the same size protein having chemotactic activity includes the steps of G-75 SEPHADEX® column, ethanol precipitation, Anti Ig column purification. The soluble peptide is capable of causing neutrophil and macrophage chemotaxis, and is substantially similar to chemotactic factor from peritoneal fluid of mammals with minimal to moderate endometriosis.

An antibody preparation specific for a chemotactic factor and a composition comprising a therapeutically effective amount of an antibody and a pharmaceutically acceptable carrier useful in the treatment of endometriosis are included in the scope of the present invention.

A method of detecting endometriosis in a mammal comprising obtaining a sample of peritoneal fluid from a mammal suspected of having endometriosis, contacting the sample with an antibody specific for chemotactic factor, forming antibody-antigen complexes comprising chemotactic factor and an antibody specific for chemotactic factor, and detecting antibody-antigen complexes is provided for in the present invention.

A method of treating a mammal having endometriosis comprising screening the mammal suspected of having endometriosis for the presence of chemotactic factor and contacting the mammal with an antibody to chemotactic factor is embodied by the present invention.

A diagnostic kit comprising an antibody for the detection of a chemotactic factor, a means for detecting chemotactic factor, and optionally containing positive and negative controls and a solid support which is useful in the detection of endometriosis is also included in the present invention.

BRIEF DESCRIPTION OF THE DRAWINGS

FIG. 3A, Protein profile for normal patients; FIG. 3B, profile for endometriosis. Column was calibrated with blue dextran of 2,000,000 molecular weight; $V_o$ soybean trypsin inhibitor of 20,000 molecular weight; and cytochrome C of 12,5000 molecular weight.

DETAILED DESCRIPTION OF THE INVENTION

Figure 1:
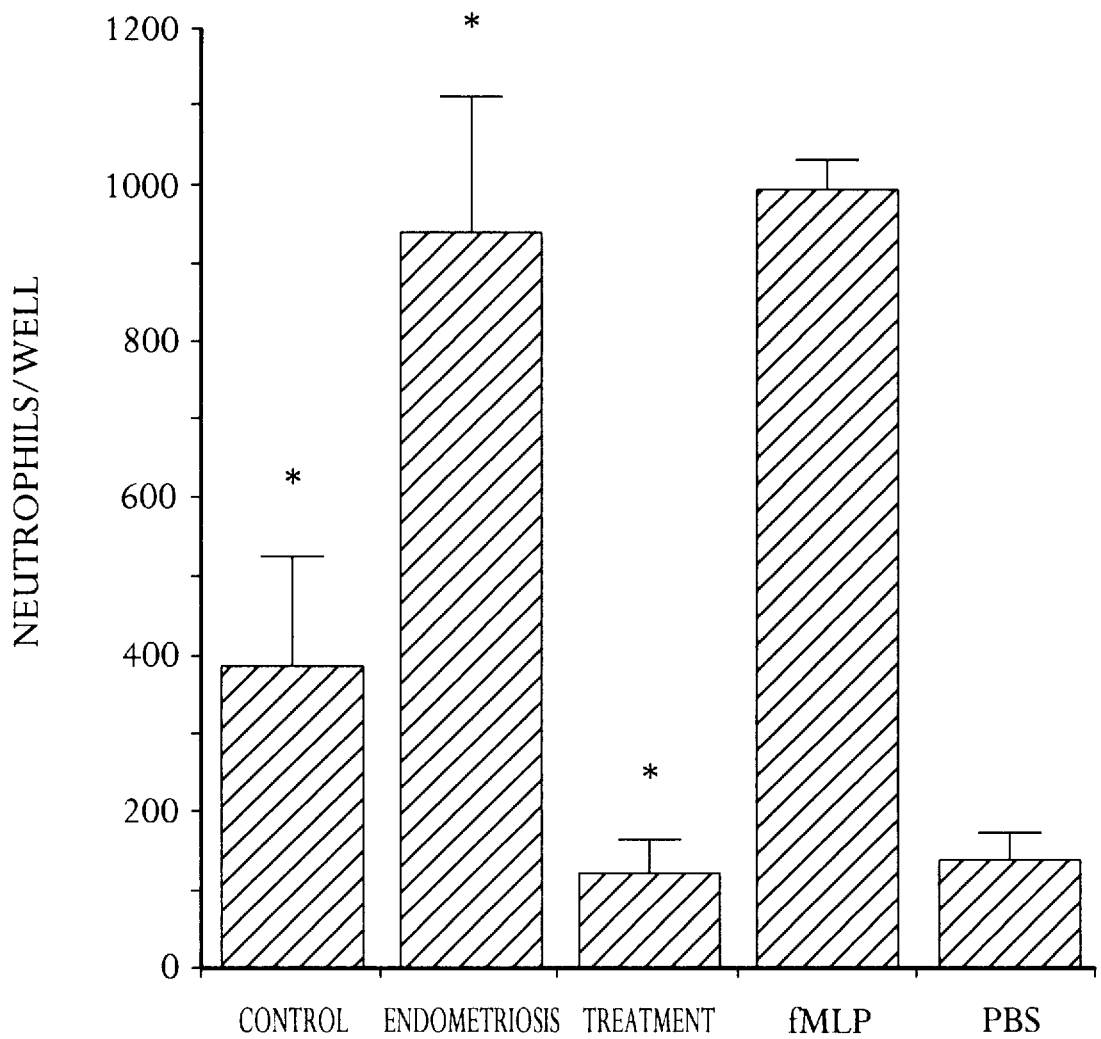
FIG. 1 sets forth a graph of chemotactic activity of peritoneal fluid to HL60-differentiated neutrophils. Peritoneal fluid from control, endometriosis, and treatment patients was analyzed for chemotactic activity with 50,000 HL60 cells differentiated to neutrophils. Background was determined with phosphate buffered saline solution. Results are expressed as number of neutrophils per well ±SD. Asterisk=p<0.001; fMLP=N-formyl-L-methionyl-L-leucyl-L-phenylalanine.

The present invention is directed to a composition comprising a soluble peptide of about 23 kD to about 29 kD, as determined by the purification protocols disclosed herein, which is capable of causing neutrophil and macrophage chemotaxis. The peptide is isolatable from peritoneal fluid of mammals with minimal to moderate endometriosis. The present invention includes peptides isolated from sources other than peritoneal fluid of mammals with minimal to moderate endometriosis which may be substantially similar to chemotactic factor from peritoneal fluid.

The composition of the present invention is referred to herein as a soluble peptide, chemotactic factor, chemotactic peptide, and the like. The soluble peptide of the present invention is about 15 kD to about 20 kD, as purified by G-75 SEPHADEX® column followed by separation on an SDS polyacrylamide gel. The soluble peptide of the present invention is more preferably about 23 kD to about 29 kD as purified by G-75 SEPHADEX® column, G-25 SEPHADEX®/Blue SEPHAROSE ® column (dextran cross-linked with epichlorohydrin/flue beaded agarose), a second G-75 SEPHADEX® column, and a Protein G column, optionally followed by HPLC purification. An alternative purification scheme which results in a chemotactic factor of the present invention includes the steps of G-75 column, ethanol precipitation, and a Protein G column.

This peptide was associated with peritoneal fluid of patients with minimal to moderate endometriosis. Accordingly, it is possible to correlate the presence of the chemotactic factor with endometriosis. Chemotactic assay results of HL-60-C15 differentiated neutrophils with peritoneal fluid from endometriosis patients revealed 933.2±172 cells per well. These results are similar to the response observed with isolated peripheral blood neutrophils, 709±13 cells per well. Similar chemotactic activity was also present when the fluid was incubated with macrophages from U937 cells, 405±72.6 cells per well.

The peptide includes peptides substantially similar, preferably identical, to chemotactic factor purified from peritoneal fluid from mammals with minimal to moderate endometriosis. The peptide includes and is not limited to recombinant, synthetic, and naturally purified peptides, and fragments of recombinant, synthetic, and naturally purified peptides, substantially similar to chemotactic factor purified from peritoneal fluid from mammals with minimal to moderate endometriosis. Peptides produced by cell culture are also included in the present invention.

Endometriosis is a complex disease that involves modifications at the anatomic level with the presence of implants present as ectopic endometrium and endometriomas distributed throughout the pelvis; it also produces modifications at the cellular and molecular level mostly observed in milder stages of the disease. The present invention discloses an increase in chemotactic activity of peritoneal fluid in patients with minimal to moderate endometriosis, which may be one of the many contributing mechanisms for the observed aseptic inflammation in the peritoneal cavity of these patients. The present invention also discloses a chemotactic factor responsible for the increased chemotactic activity of peritoneal fluid of patients with minimal to moderate endometriosis. Minimal to moderate endometriosis for use in the present invention is defined as stage I to stage III endometriosis in accordance with the American Fertility Society, Revised American Fertility Society Classification of Endometriosis. *Fertil Steril* 1985 43:351, incorporated herein by reference. Accordingly, minimal to moderate endometriosis includes mild, or stage II, endometriosis as defined by the American Fertility Society.

The cyclic variations in hormone concentrations are necessary for most of the biochemical modifications observed in the peritoneal fluid in endometriosis. The present invention suggests that an increase in chemotactic activity may be hormonally regulated and further that a state of medically induced anovulation, or suppressed ovulation, suppresses chemotaxis. The suppression of chemotaxis to values even lower than those observed for fertile controls lends support to this hypothesis. This suppression of chemotactic activity could be considered an indicator of the success of the treatment. Previous reports indicate a reduction in the pelvic inflammation associated with endometriosis after treatment with medroxyprogesterone acetate. Haney A. F., et al., *Am J Obstet Gynecol* 1988 159:450.

In the present invention, the chemotactic activity of the peritoneal fluid is demonstrated with granulocytes and macrophages. Previous reports indicate macrophages respond to chemoattractants in a manner similar to that of granulocytes. Kay G. E., et al., *Infect Immun* 1983 41:1166. Macrophages are the predominant cell type observed in the peritoneal fluid and in the cavity of patients with endometriosis. The presence of chemotactic stimulus that will increase their number may also trigger their activation: this activation may result in the release of cytokines and cytotoxic factors that may be directly responsible for the modification in the peritoneal environment.

In accordance with the present invention, a method of detecting endometriosis in a mammal comprising obtaining a sample of peritoneal fluid from a mammal suspected of having endometriosis, contacting the sample with an antibody specific for the chemotactic factor, forming antibody-antigen complexes of the chemotactic factor and antibody specific for the chemotactic factor, and detecting the antibody-antigen complexes is also disclosed. The sample may also be obtained from other bodily fluids such as and not limited to blood, urine, vaginal fluid, and the like.

The present invention is also directed to a method of treating a mammal having endometriosis comprising screening a mammal suspected of having endometriosis for the presence of the chemotactic factor, and contacting the mammal with an antibody raised to the chemotactic factor.

For purposes of the present invention, mammals include, and are not limited to the Order Rodentia, such as mice; Order Logomorpha, such as rabbits; more particularly the Order Carnivora, including Felines (cats) and Canines (dogs); and even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of the most preferred embodiments are humans.

The antibodies useful in the practice of the invention include any monoclonal antibody, polyclonal antibody, Fab fragment, and chimeric antibody, having an affinity to or binding to the naturally occurring chemotactic factor obtained from peritoneal fluid of mammals with minimal to moderate endometriosis. The method of preparing antibodies is known to those of skill in the art. Particularly, the method of Kohler and Milstein, *Nature* 1975 256:495, incorporated herein by reference, may be used to produce monoclonal antibodies for use in the invention. Polyclonal antibodies, Fab fragments, and chimeric antibodies may be produced by methods disclosed in Sambrook et al., *Molecular Cloning: A Laboratory Manual,* 2nd ed., Cold Spring Harbor Laboratory Press, Cold Spring Harbor, N.Y. (1989) and Harlow and Lane, *Antibodies, A Laboratory Manual,* Cold Spring Harbor Laboratory Press, Cold Spring Harbor, N.Y. (1981), both incorporated herein by reference.

Methods of obtaining peritoneal fluid samples for analysis include any surgical and nonsurgical technique known in the art. Surgical methods include and are not limited to biopsy, laparoscopy, and laparotomy. Nonsurgical methods include, and are not limited to peritoneal washings, peritoneal brushings, colpotomy, and vaginal ultrasound aspiration.

Methods of detecting chemotactic factor in the peritoneal fluid include all methods known in the art. These methods include and are not limited to, immunohistochemistry techniques such as immunoblotting or Western blotting, immunoperoxidase staining, fluorescein labeling diaminobenzadine and biotinylation.

The presence of chemotactic factor in peritoneal fluid is correlated with minimal to moderate endometriosis. Thus, the methods of diagnosing endometriosis are also within the scope of the invention. As provided herein, screening for chemotactic factor in peritoneal fluid of mammals suspected of having endometriosis provides a method of diagnosing endometriosis.

The present invention is also directed to a composition comprising antibody preparations specific for the chemotactic factor, wherein the antibody preparations are in solution or attached to a solid support. The solid support may be any solid support known to those of skill in the art useful in immunoassays, such as and not limited to SEPHADEX®, protein A coupled agarose beads, and the like. A composition comprising a therapeutically effective amount of an antibody to the chemotactic factor and a pharmaceutically acceptable carrier useful in the treatment of endometriosis is included in the present invention.

The compositions of the present invention may be administered alone or may generally be administered in admixture with pharmaceutically acceptable carrier selected with regard to route of administration. The antibodies and therapeutical compositions of the present invention may be administered with a pharmaceutically acceptable carrier, selected with regard to the intended route of administration and the standard pharmaceutical practice. Dosages may be set with regard to weight, and clinical condition of the mammal. The proportional ratio of antibodies to carrier will naturally depend on chemical nature, solubility, and stability, as well as the dosages contemplated. The dosages will also depend on such factors as the age and weight of the mammal. The method of administration may be by any suitable route, including and not limited to inoculation and injection, for example, intravenous, oral, intraperitoneal, intramuscular, subcutaneous, topical, and by absorption through epithelial or mucocutaneous linings, for example, nasal, oral, vaginal, rectal and gastrointestinal. The selected carrier and mode of administration of the present invention may determine the sites in the organism to which the composition will be delivered. For instance, carriers include and are not limited to topical applications which may be administered in creams, ointments, gels, oils, emulsions, pastes, lotions and the like. For parenteral administration, sterile aqueous solutions may be delivered which contain other solutes, for example, sufficient salts, glucose, or dextrose. For oral mode of administration, the present invention may be used in the form of tablets, capsules, lozenges, troches, powders, syrups, elixirs, aqueous solutions and suspensions, and the like. For oral administration, certain sweetening and/or flavoring agents may be added, which are known to those of skill in the art.

Diagnostic kits are also within the scope of this invention. Such kits include antibodies for the detection of chemotactic factor; reagents for detecting the presence of the factor, such as immunoassay type reagents; optionally positive and negative controls; optionally an absorbant detection device which may contain pre-absorbed antibodies and to which patient samples may be applied; and a means for detecting chemotactic factor when present, such as a dye.

The antibody-antigen complexes comprise the chemotactic factor and an antibody specific for the chemotactic factor. Methods of detecting the antibody-antigen complexes are known to those of ordinary skill in the art and may be found in Harlow, supra.

The present invention is further described in the following examples. These examples are not to be construed as limiting the scope of the appended claims.

EXAMPLE 1

Material and Methods

Peritoneal fluid was collected during surgical procedures, laparoscopy and one laparotomy, in patients at the Hospital of the University of Pennsylvania. Patients were classified into three groups according to anatomic findings during the procedure and clinical history; normal fertile patients who have no history of endometriosis (n=12) 19 to 37 years old (31±7 years, mean=SD) patients with minimal to moderate endometriosis, stage I to stage II endometriosis as defined by the American Fertility Society classification, The American Fertility Society, *Fertil Steril,* supra, (n=20) 20 to 40 years old (34±7 years), and patients with a previous diagnosis of endometriosis in whom the surgical procedure was performed as an evaluation of continuing medical treatment for the disease (n=8) (32±1 years). All treatments had been initiated at least 6 months before the surgical procedure and were still being administered when the laparoscopy was performed. This group included patients receiving medical suppression of endometriosis (danazol, progestational agents (medroxyprogesterone acetate), or combination, progestins and estrogens, oral contraceptives).

All peritoneal fluid samples were collected by aspiration during the proliferative phase of the menstrual cycle, the stage in a normal menstrual cycle which is under the influence of estrogen. The aspirate was obtained from the posterior and anterior cul-de-sac of the peritoneum before any other intervention, to avoid blood contamination. After aspiration into a sterile syringe, samples were centrifuged at 2000 g for 10 minutes at 4° C. to remove any possible contaminating blood; samples with gross blood contamination were discarded. After centrifugation the supernatant was aliquoted and immediately processed in the chemotaxis assay or stored at −70° C. for evaluation at a later time. The study protocol was approved by the University of Pennsylvania Investigational Committee on the Study of Human Beings.

CHEMOTAXIS ASSAY

The chemotaxis assay was performed by means of a 48-well chemotactic chamber (Neuroprobe, Cabin John, Md.) with a 5 $\mu$m pore polycarbonate filter (Nucleopore, Pleasanton, Calif.) as described by Lee Y. H., et al., *Endocrinology* 1989 125:3022, incorporated herein by reference. Samples, in 30 $\mu$l, were applied to the lower chamber and incubated for 30 minutes at 37° C. in humidified 5% carbon dioxide and 95% air atmosphere. After incubation, 50 $\mu$l of a cell suspension (containing $\geq$50,000 HL-60-C15 differentiated neutrophils) was added to the upper chamber, and the chemotaxis chamber was incubated for another hour under the same conditions. HL60-C15 cells were cultured in Roswell Park Memorial Institute (RPMI) media with 10% heat-inactivated fetal calf serum and differentiated to neutrophils by adding 1.25% dimethyl sulfoxide (Sigma, St. Louis) for 7 days, as described by Howe R. S., et al., *Exp Hematol* 1990 18:299, incorporated herein by reference. The chemotaxis assay was repeated for each patient sample with neutrophils isolated through a Percoll gradient (Pharmacia, Piscataway, N.J.) from the patients' peripheral blood; and U937 cells, a human histiocytic cell line that can be differentiated to macrophages and has been shown to display chemotactic activity by Sundstromm C, et al., *Int J. Cancer* 1976 17:565 and Kay G. E., et al., supra. Samples testing neutrophils and U937 cells were processed according to the methods set forth above for HL-60-C15 cells with the exception that U937 cells were cultured in Roswell Park Memorial Institute (RPMI) media with 10% serum and stimulated with 1 mmol/L dibutyryl cyclic adenosine 2'-monophosphate (Sigma) for 48 hours to induce their transformation into macrophages. Chemotactic responses with either of the cell types were comparable, as demonstrated by Howe R. S., et al., supra and Lee Y. H., et al., supra. After 1 hour of incubation the polycarbonate membrane was washed in phosphate-buffered saline solution (Gibco, Grand Island, N.Y.), fixed in methanol and stained with Wright-Giemsa (Hemacolor, EMI Diagnostics, Biggstown, N.J.). A known chemotactic peptide, N-formyl-L-methionyl-L-leucyl-L-phenylalanine (Sigma) was used as positive control, and negative controls included phosphate-buffered saline solution and 10 mmol/L Tris hydrochloric acid buffer, pH 7.4 (T-10). Chemotaxis was assessed by counting the number of neutrophils that had migrated to the bottom side of the filter. Chemotactic activity for each sample was expressed as mean=SD. Statistical significance was calculated by means of one-way analysis of variance. A p value of ≦0.05 was considered significant. This experiment was repeated using isolated peripheral blood neutrophils and U937 cells.

Figure 2:
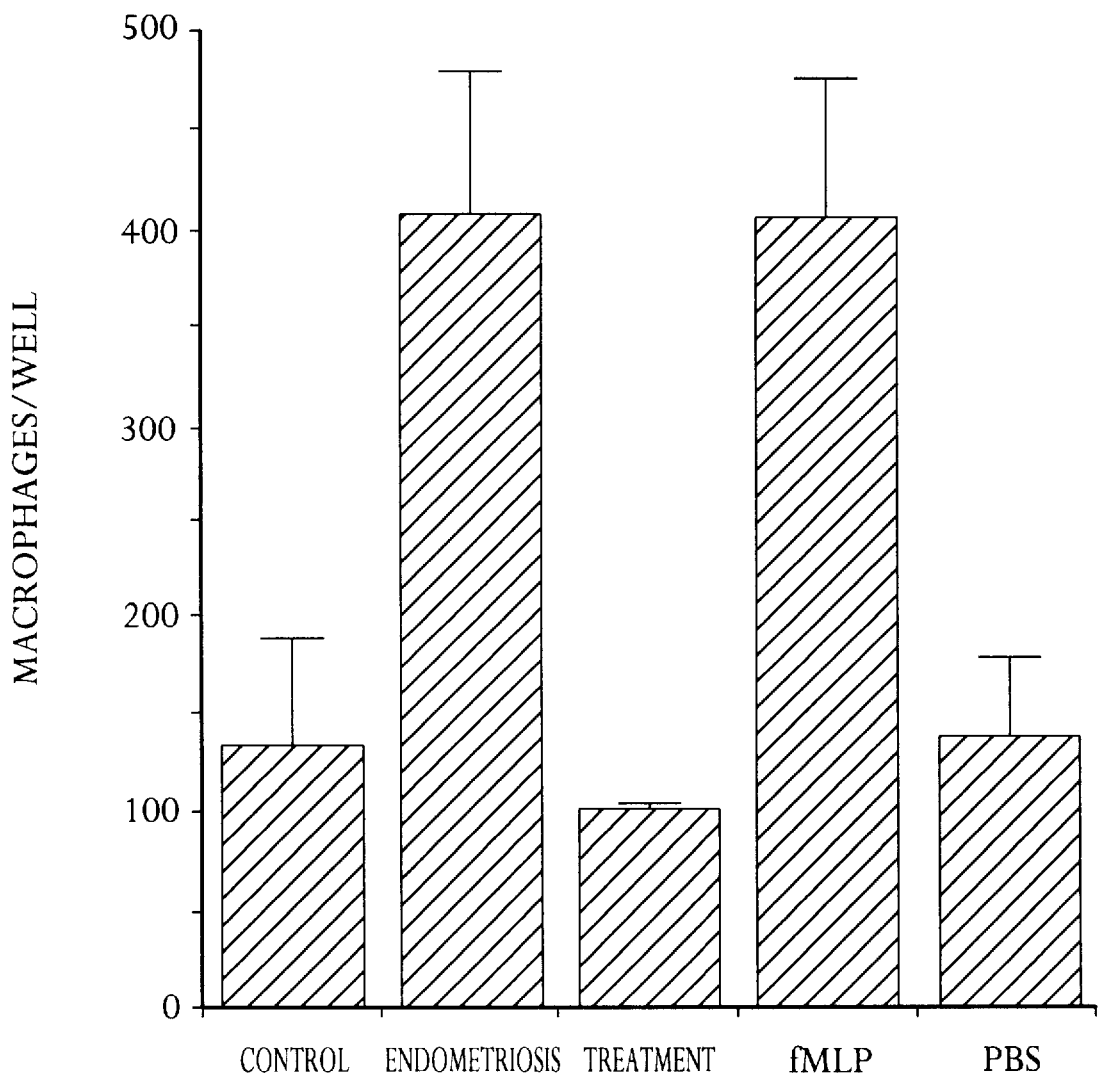
FIG. 2 is a graph of chemotactic activity of peritoneal fluid to macrophages. U937 cells were differentiated to macrophages as described in Material and methods and used at a concentration of $1 \times 10^6$ cells per milliliter. Results are expressed as number of macrophages that migrated to lower side of membrane per well ±SD. Positive and negative controls are as described in FIG. 1. fMLP=N-formyl-L-methionyl-L-leucyl-L-phenylalanine; PBS=phosphate buffered saline solution.

Peritoneal fluid from patients with minimal to moderate endometriosis exhibited chemotactic activity for isolated peripheral blood neutrophils, HL60-differentiated neutrophils, and U937 cells. The results presented in FIG. 1 indicate that the peritoneal fluid from patients with minimal to moderate endometriosis display chemotactic activity for HL60 neutrophils approximately equal to that seen with the positive control (N-formyl-L-methionyl-L-leucyl-L-phenylalanine). Peritoneal fluid chemotactic activity from normal patients was significantly different from the endometriosis group, 384.6±140 versus 933.2±172 ($p<0.001$), respectively. It is interesting that the fluid of patients undergoing treatment demonstrated the lowest activity, 114±45 ($p<0.001$ when compared with that of patients with minimal to moderate endometriosis). These results are similar to the response observed with isolated peripheral blood neutrophils, which was 709±13 cells per well in the endometriosis group, 289±29 for the control group, and 145±20 for the treatment group. The data in FIG. 2 indicate that this chemotactic activity was also present when the fluid was incubated with macrophages from U937 cells and that this activity was similar to that observed for neutrophils, which was 405±72.6 for the endometriosis group, 133±56.5 for the control group, and 100±2 for the treatment group.

EXAMPLE 2

Chemotactic Factor Partial Purification

To further investigate the nature of the chemotactic activity observed in the peritoneal fluid, pools of six to ten patient samples were passed through a G-75 superfine SEPHADEX® column in 10 mmol/L Tris-hydrochloric acid buffer, pH 7.4, which had been previously calibrated with known protein standards (blue dextran, bovine serum albumin, ovalbumin, soybean trypsin inhibitor, and cytochrome C, Sigma). Protein profiles of the eluant were monitored by a spectrophotometer (absorbance at 280 nm). The major protein peaks were assayed for chemotactic activity. Fractions displaying chemotactic activity and their equivalents from the control group were analyzed by 12% sodium dodecyl sulfate polyacrylamide gel electrophoresis under standard reducing conditions. Gels were fixed and stained with comassie blue. The protein band in the low molecular weight range in the endometriosis samples was cut and electroeluted with the Isco electroelutor-concentrator (Isco, Lincoln, Nebr.). Gel pieces from the low molecular weight range were placed in a sample cup and eluted with 3-(cyclohexylamine)-1-propane-sulfonic acid buffer, pH 11, with a concentration of 5 mmol/L in the inner chamber, and 25 mmol/L in the outer chamber, and 2.5 mmol/L in the sample cup. Electroelution was performed for 60 minutes at 8 watts and the eluted protein was tested for chemotactic activity by means of macrophages differentiated from U937 cells.

Figure 3A:
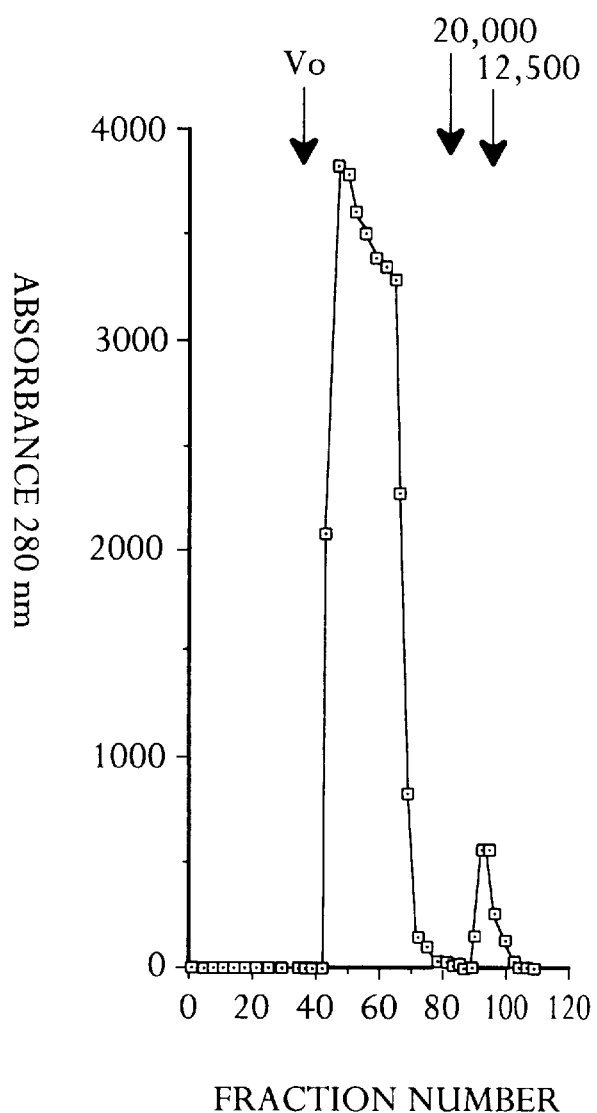
FIGS. 3A–3B exhibit protein profiles of peritoneal fluid from control and endometriosis patients. Equal amounts of total protein were applied to a G-75 superfine SEPHADEX® column and eluted with buffer. The 280 nm absorbance of each fraction was determined.
Figure 3B:
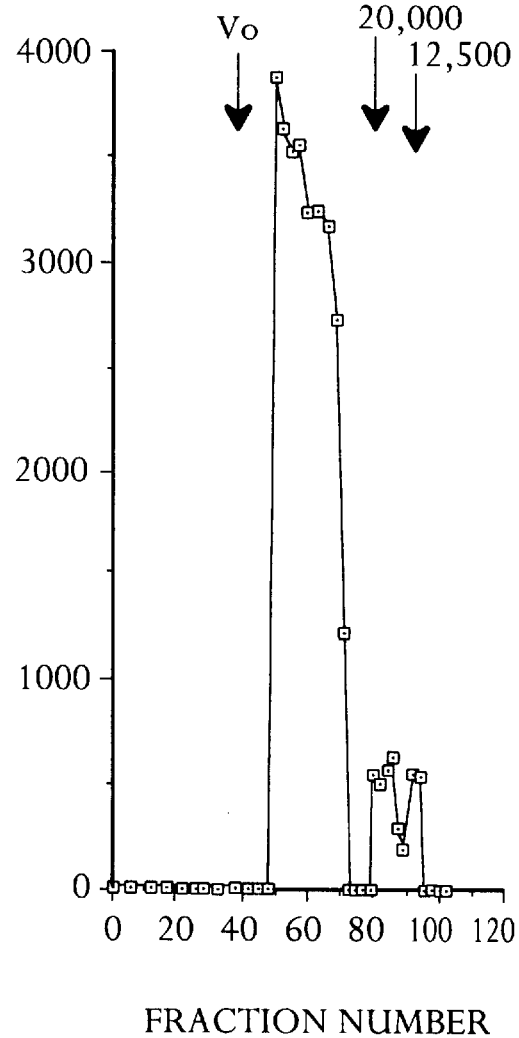
Figure 4:
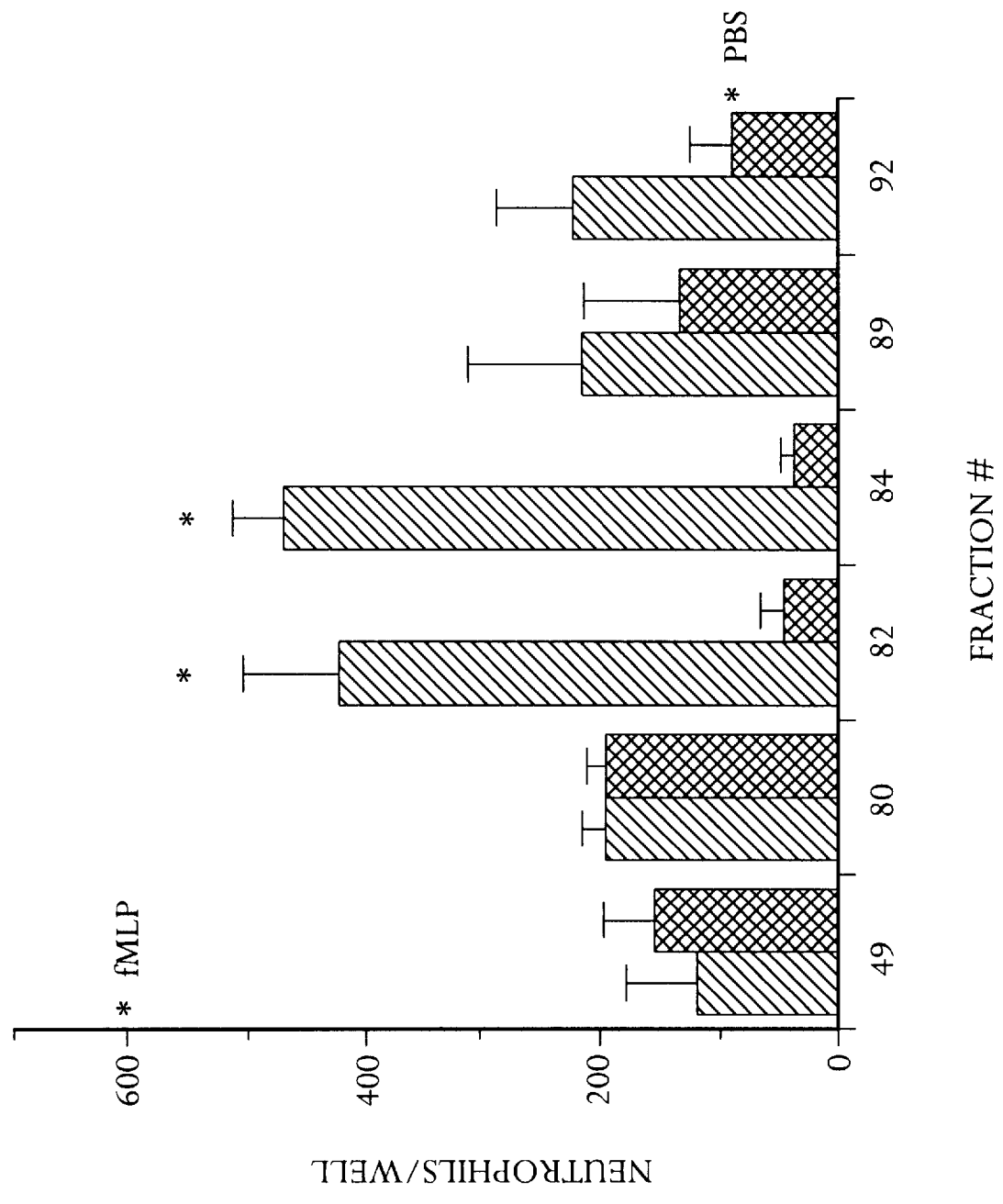
FIG. 4 displays chemotactic activity of peritoneal fluid after fractionation in a G-75 SEPHADEX® column. A 30 μl aliquot of each fraction was assayed in triplicate for chemotactic activity. Hatched bars=endometriosis samples; Solid bars=control samples. Results are expressed as number of neutrophils per well ±SD. Value for positive control (N-formyl-L-methionyl-L-leucyl-L-phenylalanine, $10^{-6}$ mol/L) of 592±88.8 and background activity phosphate buffered saline solution (PBS) of 112±58 are shown. Asterisk=p<0.001 between control and endometriosis fractions.

Examination of the protein profile of both endometriosis and fertile normal patients after separation through a G-75 SEPHADEX® column revealed some differences between groups. Both groups displayed a similar profile, with the majority of the protein content of being of high molecular weight and a small peak of protein in the low-molecular-weight range. However, samples from patients with endometriosis had an additional protein peak of low molecular weight (FIG. 3A and B). Protein peaks of both groups were tested for chemotaxis; the data in FIG. 1 indicate that the activity of the first protein peak that corresponded to proteins of 60 kD and higher molecular weights did not demonstrate any difference. Peritoneal fluid from endometriosis patients had the majority of its chemotactic activity associated with the fractions corresponding to the additional protein peak of low molecular weight, about 15 kD to about 20 kD. The activity displayed by these fractions was significantly different from that of the fertile group.

Figure 5:
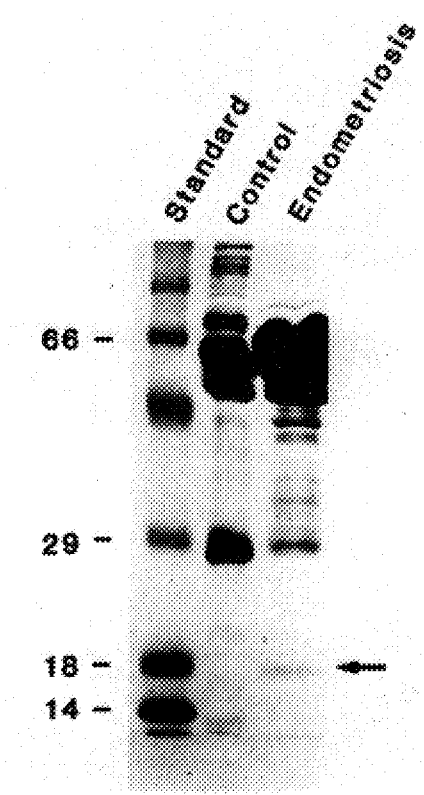
FIG. 5 displays sodium dodecyl sulfate polyacrylamide gel electrophoresis analysis of chemotactic fractions from peritoneal fluid of patients with endometriosis and their equivalents from disease-free controls. A total of 20 μg of protein was loaded into each lane. Arrow=protein and of approximately 20 kD present only in endometriosis fractions.

Fractions displaying chemotactic activity from the endometriosis group (fractions 82 and 84) and their equivalents from disease-free patients were further analyzed by sodium dodecyl sulfate polyacrylamide gel electrophoresis under reducing conditions. The gel was stained with comassie blue, and analysis of these fractions demonstrated a protein band with an estimated molecular weight of about 20 kD, which was present in the samples from patients with minimal to moderate endometriosis (FIG. 5). This protein was electroeluted and tested for chemotactic activity with macrophages, demonstrating a chemotactic response three times higher than background (231.1±44 versus 75.7±11).

The results indicate that the peritoneal fluid from patients with endometriosis has increased chemotactic activity for neutrophils and macrophages. Endometriosis samples have an additional peak of protein in the range of about 15 kD to about 20 kD after gel-sieving chromatography on a G-75 SEPHADEX® column, which is responsible for the chemotactic activity observed in the fluid of these patients. Analysis of the chemotactic fractions by sodium dodecyl sulfate polyacrylamide gel electrophoresis revealed the presence of a protein band with an estimated molecular weight of about 20 kD only in the endometriosis samples, which is responsible for this activity. The results also indicate that patients with medical suppression as treatment for endometriosis have the lowest chemotactic activity.

EXAMPLE 3

Materials and Methods

Peritoneal fluid was collected by aspiration during laparoscopy from posterior cul de-sac of female patients at the Hospital of the University of Pennsylvania. The study protocol was approved by the University of Pennsylvania Investigational Committee on the Study of Human Beings.

Peritoneal fluid was collected from the posterior cul de sac of 84 women undergoing laparoscopy between February 1992 and June 1993. The patients ranged in age from 15–39. Patients were divided into two main categories according to the findings at laparoscopy; group I—patients without noted endometriosis (n=39), group II—patients with endometriosis (n=45). Group II was subdivided into three sections according to the AFS classification of endometriosis, *Fertil Steril*, supra; stage I–II (n=41), stage III (n=2), stage IV (n=2). The aspirate was collected prior to any intervention into a sterile syringe, placed on ice and centrifuged at 2000 g for 10 minutes. The supernatant was aliquoted into 3 cc vials and stored at −70° C.

CHEMOTAXIS ASSAY

The chemotaxis assay was performed on each of the samples by a quantitative assay developed by Lee, Y. H., et al., supra, incorporated herein by reference. A chemotactic chamber having a polycarbonate filter (Neuroprobe, Cabin John, Md.) was used. U937 cells, a macrophage stem cell line, were grown in RPMI (Gibco, Great Island, N.Y.) plus 10% bovine serum albumin (JRH, Lenexa, Kans.) 5% Glutamate (Gibco) and 5% penicillin/ streptomycin, PCN/ Strep, (Gibco). Differentiation of the U937 into macrophages was stimulated with the addition of $N^{6}2^{1}$-O-Dibutyryl-adenosine $3^{1}5^{1}$ cyclic monophosphate (Sigma) per 10 cc for 48 hours.

Figure 8:
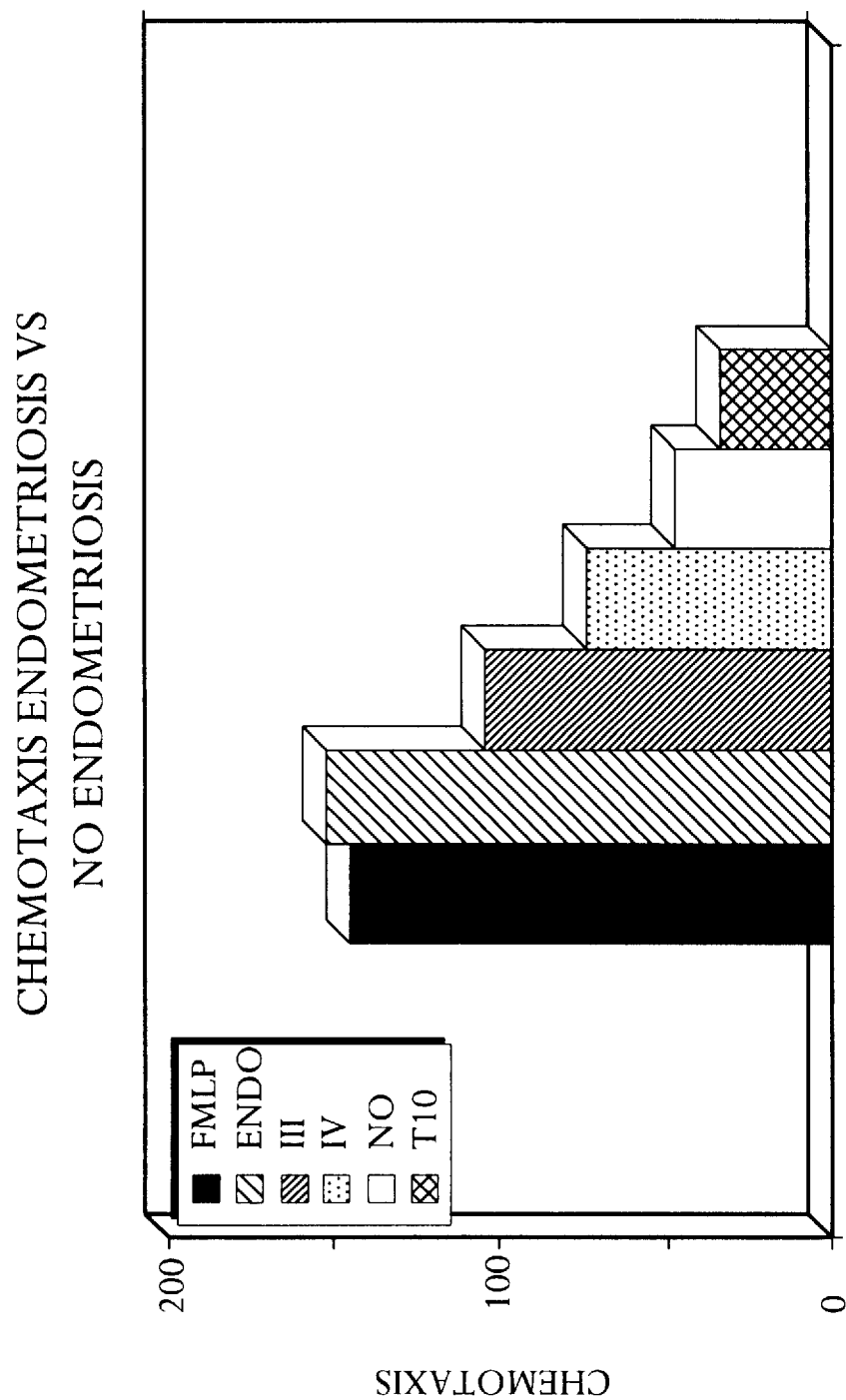
FIG. 8 is a graph of chemotactic activity of endometriosis and non-endometriosis peritoneal fluid. N-formyl-L-methionyl-L-leucyl-L-phenylalanine, FMLP, is a known chemotactic positive control, ENDO—stage I–II patients, III—stage III patients, IV—stage IV patients, NO—patients without endometriosis, and T-10—10 mmol/L Tris pH 7.4, negative control.

The peritoneal fluid from patients with endometriosis, group II, had significantly increased chemotactic activity (mean=148±59) over the peritoneal fluid of patients without endometriosis, group I, (mean=48±26) and over the negative controls (mean=25±15) p<0.001. The chemotactic activity of group II increased beginning with stage IV (mean=75), stage III (mean=105) and greatest with stage III (mean=153), see FIG. 8. Three of the 39 samples in group I displayed chemotactic activity comparable with that of group II or positive controls. All of the samples in group II displayed chemotactic activity similar to positive controls.

PURIFICATION

Figure 6:
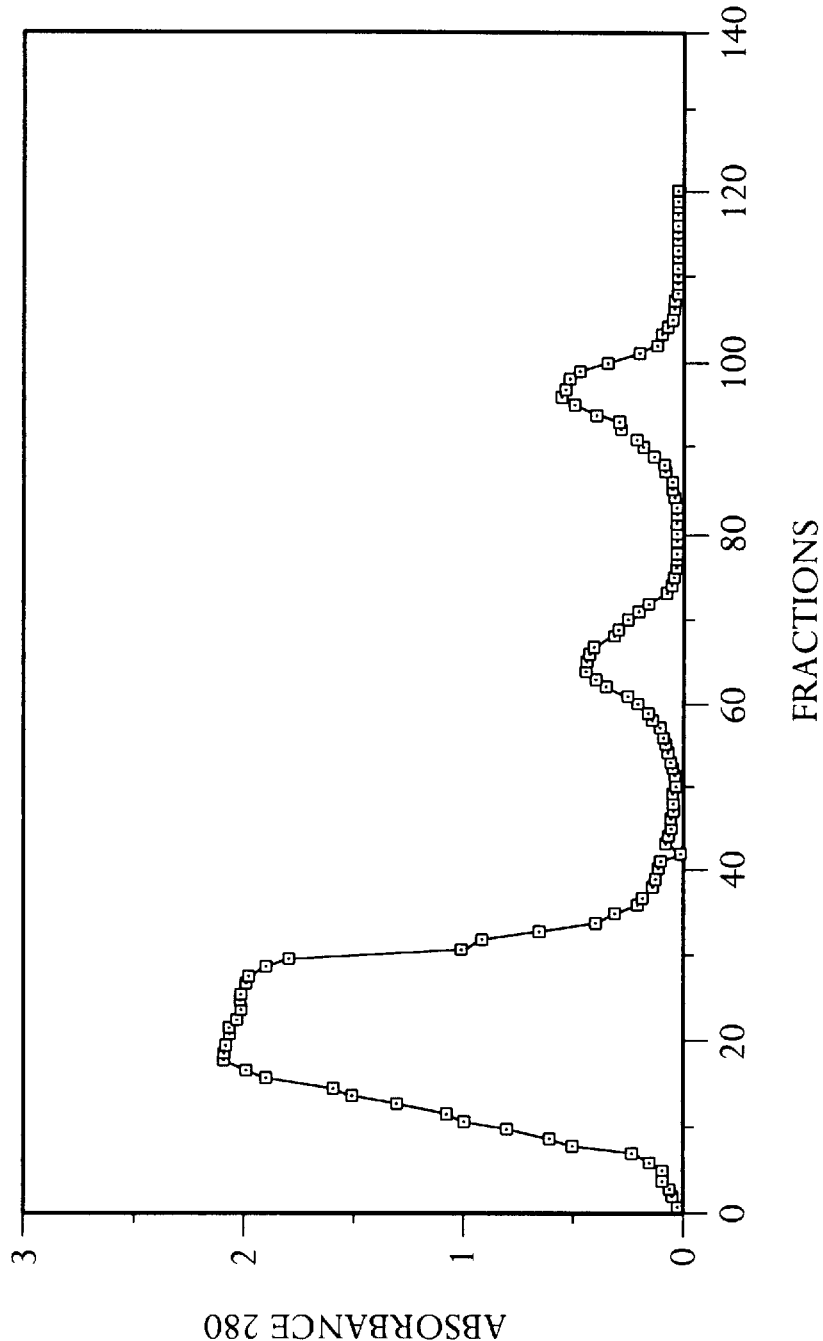
FIG. 6 exhibits a protein profile of peritoneal fluid from endometriosis patients following G-75 SEPHADEX® column purification. The purification resulted in three peaks: 90-60 kD molecular weight, 45-20 kD molecular weight, and 15-12 kD molecular weight. Equal amounts of total protein were applied to a G-75 superfine SEPHADEX® column and eluted with buffer. The 280 nm absorbance of each fraction was determined.

Peritoneal fluid from each patient was passed through a G-75 SEPHADEX® (Sigma) column in 10 mm/L tris-hydrochloride buffer (T-l0), pH 7.4, which was previously calibrated with known protein standards. The protein profile was monitored by a spectrophotometer (absorbance at 280 nm), FIG. 6. The purification resulted in three peaks: about 90-60 kD molecular weight, about 45-20 kD molecular weight, and about 15-12 kD molecular weight. The chemotaxis assay was performed on a sample of each peak. Peak 2, 45-20 kD, consistently displayed chemotactic activity.

Figure 9:
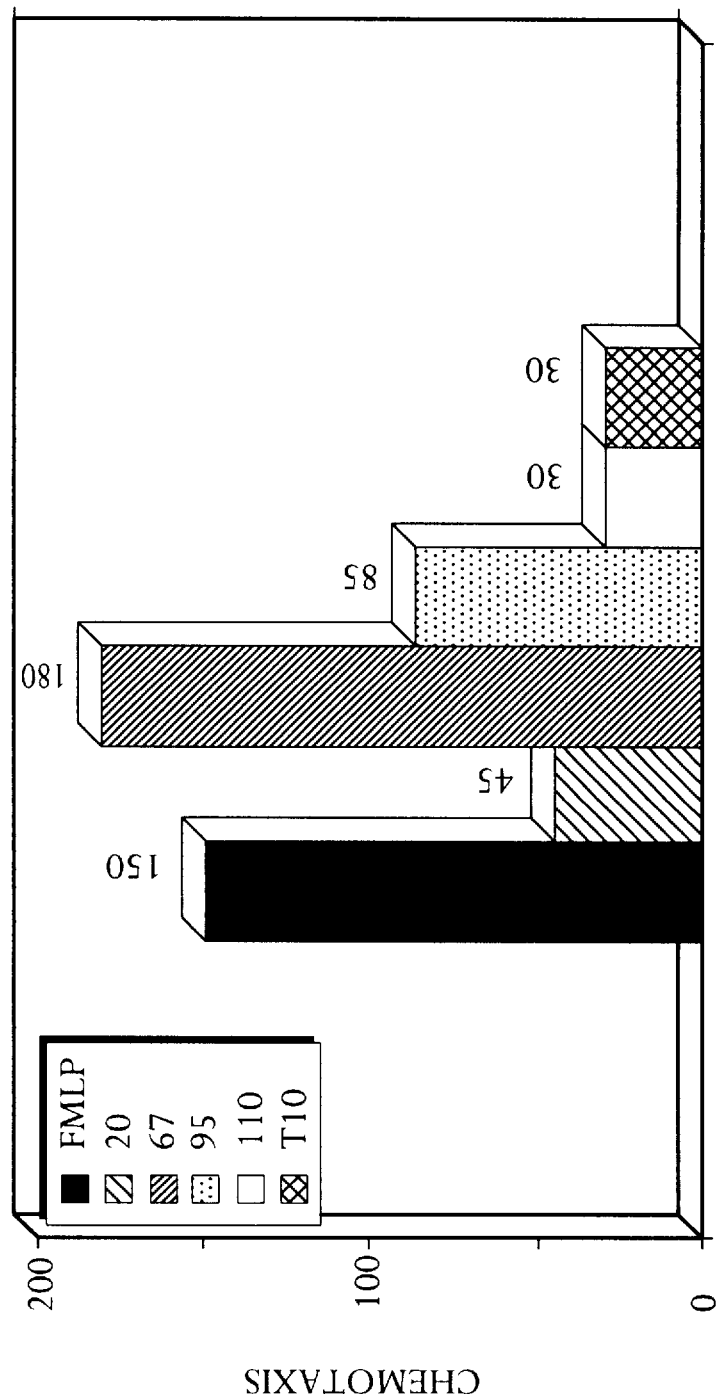
FIG. 9 is a graph of chemotactic activity of G-75 SEPHADEX® column fractions. The box in the upper left corner of the graph sets forth the fractions numbers of the G-75 SEPHADEX® column purification tested which correspond to the fractions in FIG. 6. N-formyl-L-methionyl-L-leucyl-L-phenylalanine, FMLP, is a known chemotactic positive control and T-10, 10 mmol/L Tris pH 7.4, is a negative control. The numbers above each bar represent the mean.

Chemotactic activity of the G-75 SEPHADEX® column fractions is displayed in FIG. 9. The fraction numbers, displayed in a legend in the left corner of FIG. 9 correspond to the fraction numbers in FIG. 6. The mean for FMLP was 150, Fraction 67 provided the highest chemotactic activity of the samples (mean=180), followed by Fraction 95 (mean=85), Fraction 20 (mean=45), and the negative control, T-10 and fraction 110 (mean=30).

Figure 7:
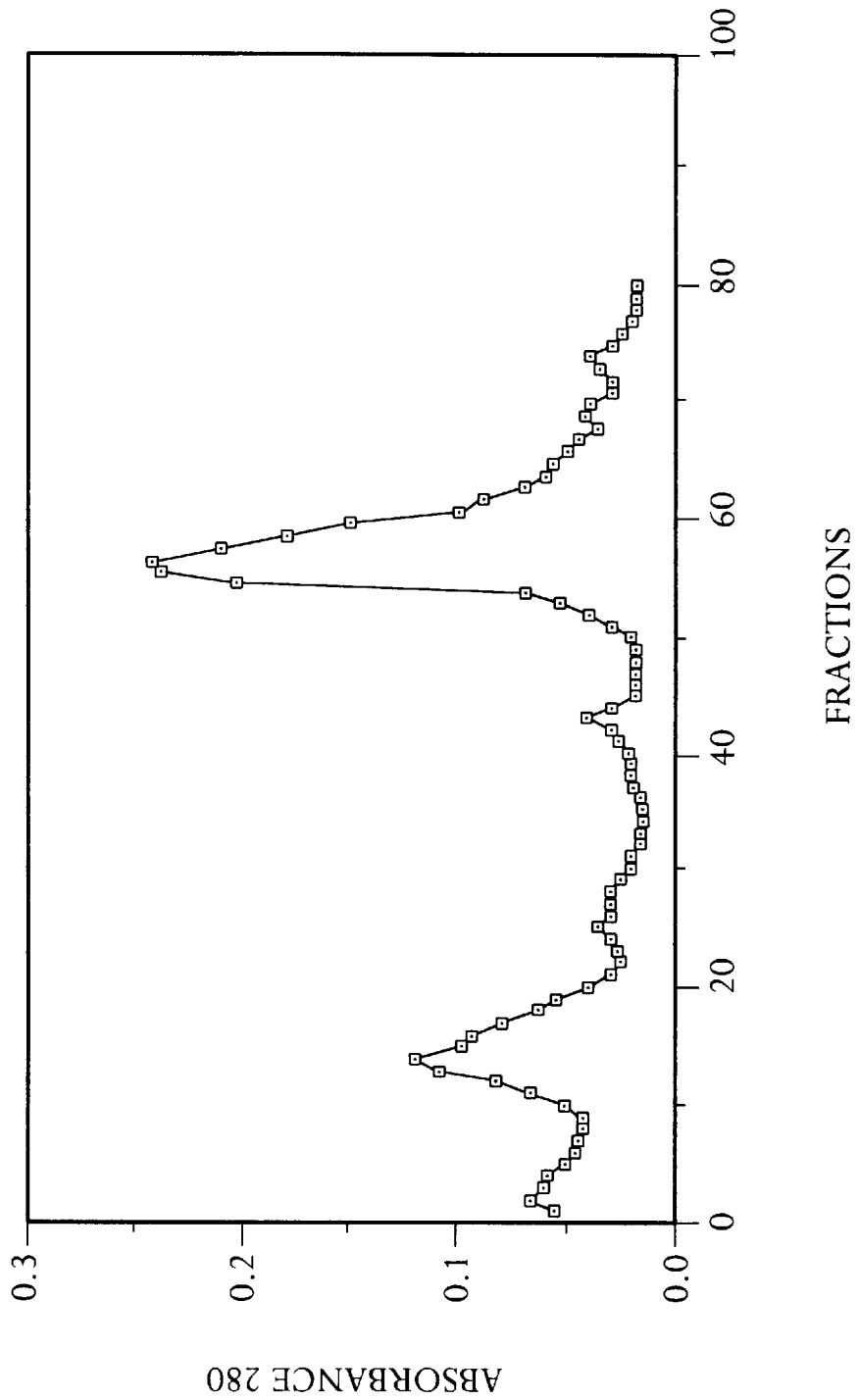
FIG. 7 displays a protein profile of peritoneal fluid from endometriosis patients following G-25 SEPHADEX®/Blue SEPHAROSE® column purification. The purification resulted in two peaks: 90-60 kD molecular weight, 45-20 kD molecular weight Equal amounts of total protein were applied to a G-25 SEPHADEX®/blue SEPHAROSE® column and eluted with buffer. The 280 nm absorbance of each fraction was determined.

Peak 2 samples of three patients (stage I–II) were pooled and concentrated by a speed vacuum and analyzed on a G-25 SEPHADEX®/Blue SEPHAROSE® (Sigma) column in T-10. 2 Molar NaCl (in a volume equivalent to 80% of the sample volume) was added to fractions collected after the bed volume to reveal one chemotactic peak, FIG. 7. This peak provided the chemotactic protein of about 23 to about 29 kD.

Figure 10:
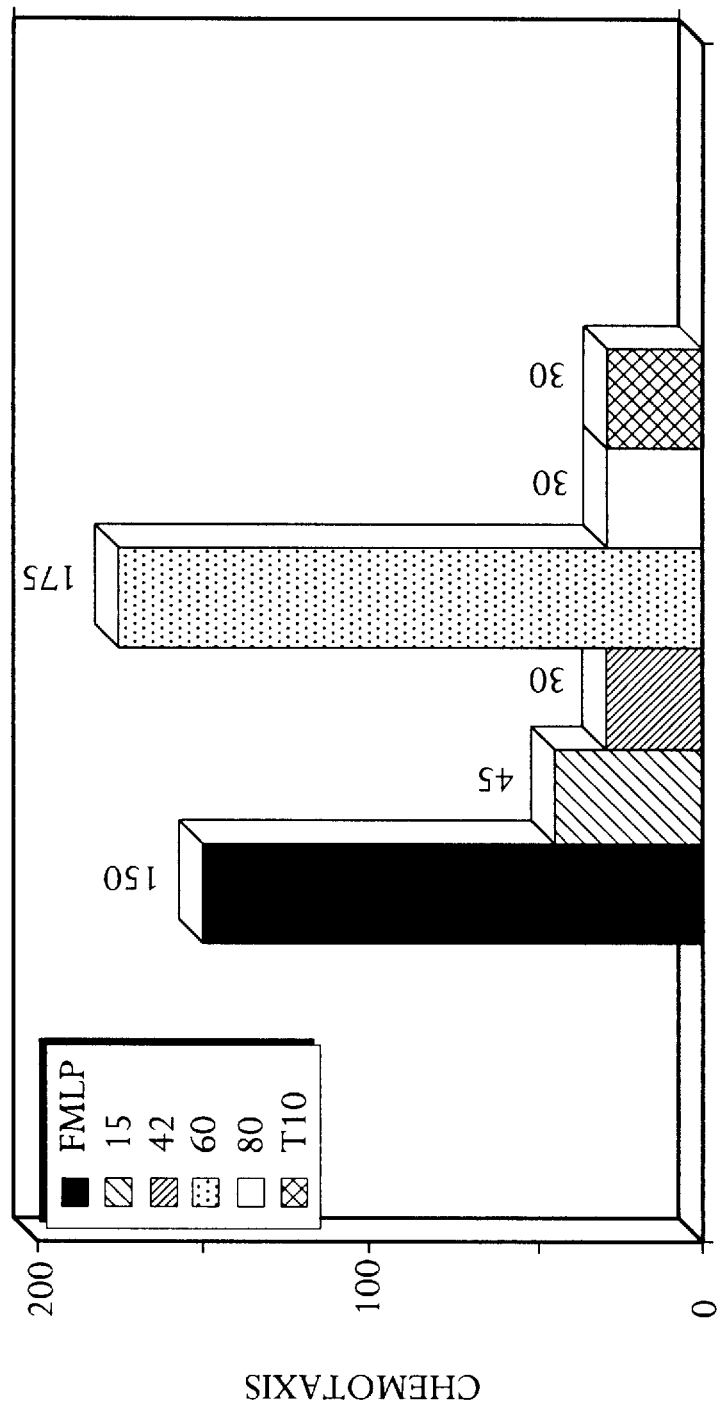
FIG. 10 is a graph of chemotactic activity of G-25 SEPHADEX®/Blue SEPHAROSE® column fractions. The box in the upper left corner of the graph sets forth the fractions numbers of the G-25 SEPHADEX®/Blue SEPHAROSE ® column purification tested which correspond to the fractions in FIG. 7. N-formyl-L-methionyl-L-leucyl-L-phenylalanine, FMLP, is a known chemotactic positive control and T-10, 10 mmol/L Tris pH 7.4, is a negative control. The numbers above each bar represent the mean.

Another chemotactic assay was performed on the fractions identified in FIG. 7. Chemotactic activity of these fractions is set forth in FIG. 10. The fraction numbers, displayed in a legend in the left corner of FIG. 10 correspond to the fraction numbers in FIG. 7. The mean for FMLP was 150, Fraction 60 provided the highest chemotactic activity of the samples (mean=175), followed by Fraction 15 (mean=45), Fractions 42, 80, and the negative control, T-10 (mean=30).

Concentrated samples of the chemotactic factor, resulting after G-75 SEPHADEX® and samples after G-25 SEPHADEX®/Blue SEPHAROSE® column purification, were run on a 12% SDS—polyacrylamide gel electrophoresis under reducing conditions.

For SDS PAGE, to each sample was added 5 $\mu$l of 0.1% bromophenol blue (Na$^+$ salt) and 2X final sample buffer (FSB) in an amount equal to the volume of the sample. 2X FSB is prepared as follows:

| | |
|---|---|
| water | 0.5 ml |
| Tris HCl (0.5M, pH 6.8) | 2.5 ml |
| glycerol | 2.0 ml |
| SDS (10%) | 4.0 ml |
| β-mercaptoethanol* | 1.0 ml |

*for non-reducing gel, omit β-mercaptoethanol

Standards contained 20 $\mu$l standard:20 $\mu$l 2X FSB. Each sample was a total volume of 30 $\mu$l. Samples and standards were vortexed, heated at 95° C. for 2 minutes. The SDS gels were then stained with comassie blue.

Figure 11:
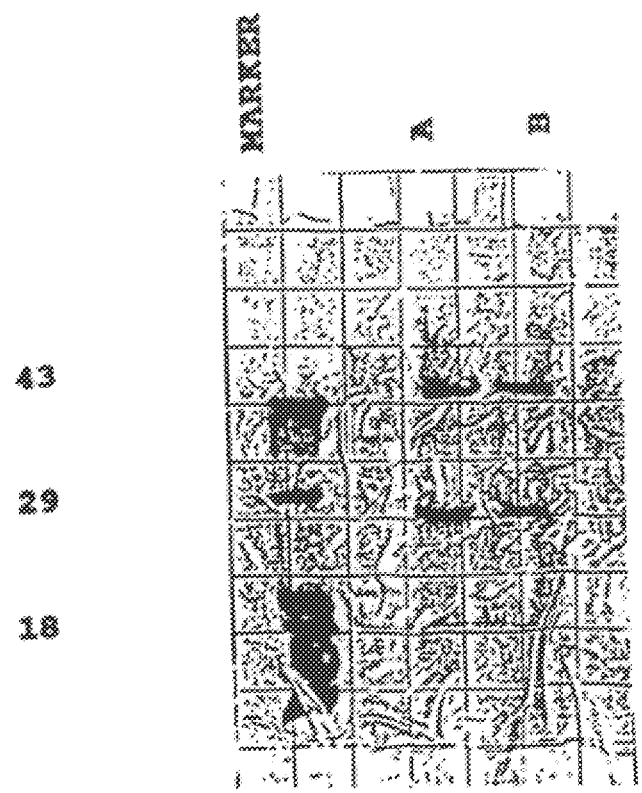
FIG. 11 is a gel stained with comassie blue. Lanes A and B represent samples which have been purified by G-75 SEPHADEX® column, G-25 SEPHADEX®/Blue SEPHAROSE®, and G-75 SEPHADEX® columns; Marker represents the molecular weight marker lane.
Figure 12:
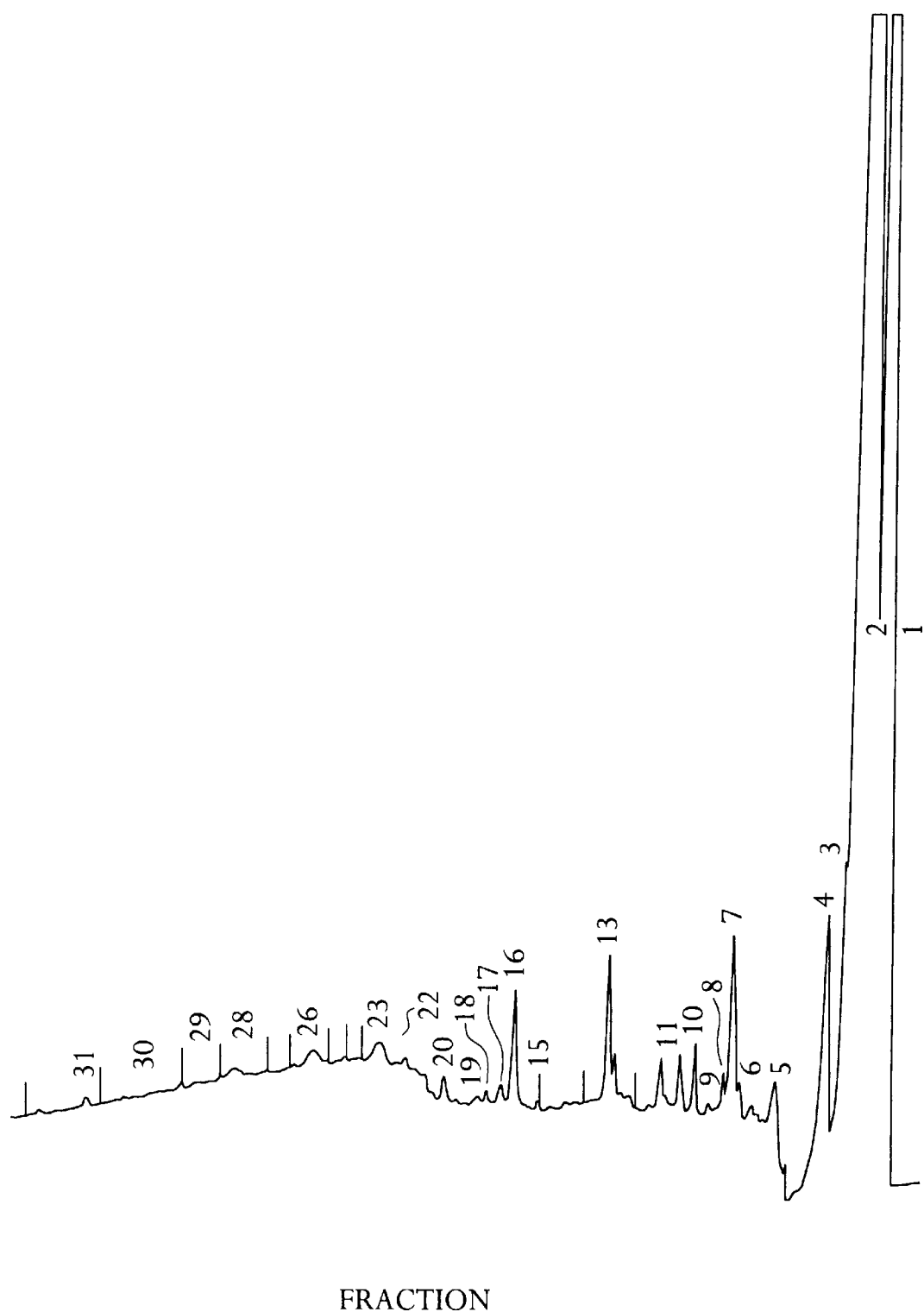
FIG. 12 displays the results of HPLC, two of the fractions, measured at $absorbance_{215}$, were found to be chemotactic.

The G-25 SEPHAREX/Blue SEPHAROSE® fraction was run on a second G-75 SEPHADEX® column. FIG. 11 reveals the results of the G-25 SEPHADEX/Blue SEPHAROSE® fraction run on a second G-75 SEPHADEX® column. Comassie blue staining revealed two bands, about 45 to about 55 kD and about 28 to about 29 kD. The concentrated samples were then analyzed by a Protein G column and HPLC. The HPLC results revealed two fractions having chemotactic activity, FIG. 12.

Concentrated samples of the chemotactic fraction from G-25 SEPHADEX/blue SEPHAROSE® columns were also analyzed on a G-75 SEPHADEX® column. The protein peak from this column, measured by absorbance at 280 nm, was run on a 12% SDS gel and stained with comassie blue.

Chromatography, electrophoresis, and chemotaxis assay, set forth above, verified that the 23–29 kD band identified as peak 2 in FIG. 7, contained the chemotactic factor.

EXAMPLE 4

Using the samples obtained for Example 3 above, G-75 SEPHADEX® column purification was performed as described above and the samples were precipitated in ethanol. All equipment and 100ETOH were placed in –20° C. to chill. Two concentrated samples of the chemotactic fraction from the G-75 SEPHADEX® column were placed in a chilled beaker. Cold ETOH was slowly added to the samples until maximum precipitation was noted at =80% of sample volume. The sample was then centrifuged at 2000 g for 10 minutes at 10° C. The supernatant and pellet were separated and the pellet was resuspended in T-10 at pH 7.4.

The chemotaxis assay was performed on the supernatant and on the pellet. Positive chemotaxis noted only in the reconstituted pellet portion, as set forth in Table 1.

TABLE 1

| Sample | Mean |
|---|---|
| T-10 | 25 |
| G-75 | 160 |
| Supernatant | 50 |
| Pellet | 110 |
| FMLP | 175 |

The ethanol precipitated protein in T-10 was then run over a Protein G column (Spectra Gel, Spectrum) and all fractions collected. The samples were concentrated and remained chemotactic, as set forth in Table 2.

TABLE 2

| Sample | Mean |
|---|---|
| T-10 | 30 |
| G-75 | 185 |
| After Protein G column | 170 |
| FLMP | 195 |

Figure 13:
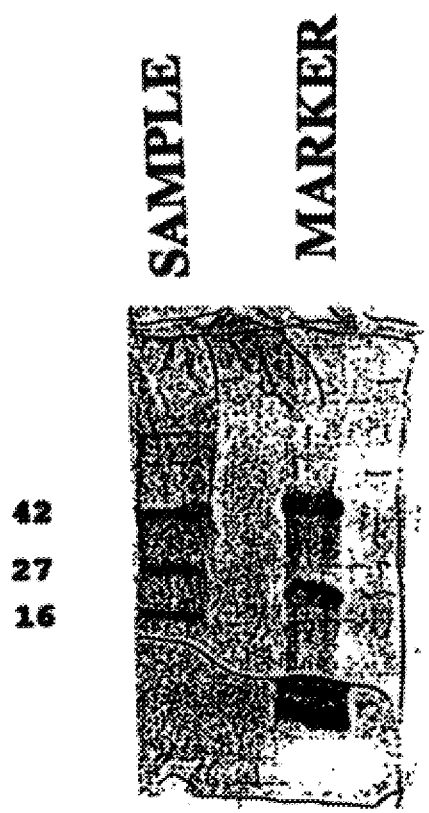
FIG. 13 displays the results of a comassie stained gel. The sample lane represents the G-75, EtOH precipitated, Protein G purified chemotactic factor, Marker represents the molecular weight marker lane.

The concentrated sample was run on a 12% SDS gel and stained with comassie blue. Three bands resulted from the G-75, ethanol precipitated, Protein G purified protein, about 42 kD, about 27 kD, and about 16 kD, see FIG. 13.

Various modifications of the invention in addition to those shown and described herein will be apparent to those skilled in the art from the foregoing description. Such modifications are also intended to fall within the scope of the appended claims.

What is claimed:

1. A purified soluble peptide of about 27 kD as determined by purification on a.) a column of dextran cross-linked with epichlorohydrin, b.) a column of dextran cross-linked with epichlorohydrin/blue beaded agarose, c.) a column of dextran cross-linked with epichlorohydrin, d.) an Anti Ig column, and e.) SDS polyacrylamide gel electrophoresis, said peptide isolated from peritoneal fluid of mammals with minimal to moderate endometriosis, said peptide having chemotactic activity to neutrophils and macrophages.

2. A purified soluble peptide of about 27 kD, having chemotactic activity to neutrophils and macrophages, isolated from peritoneal fluid of mammals having minimal to moderate endometriosis, as determined by purification by:
   a) obtaining a sample of body fluid suspected of containing said peptide;
   b) purifying said sample on a column of dextran cross-linked with epichlorohydrin;
   c) pooling the 50-20 kD molecular weight fractions thereby forming a 50-20 kD pooled sample;
   d) purifying said 50-20 kD pooled sample on a column of dextran cross-linked with epichlorohydrin/blue beaded agarose, thereby obtaining a second pooled sample;
   e) purifying said second pooled sample on a second column of dextran cross-linked with epichlorohydrin, thereby obtaining a third pooled sample; and
   f) purifying said third pooled sample on an Anti Ig column to obtain said soluble peptide.

3. A purified soluble peptide of about 27 kD, said peptide having chemotactic activity against neutrophils and macrophages and said peptide isolated from peritoneal fluid of mammals with minimal to moderate endometriosis, as determined by purification by:
   a) obtaining a sample of body fluid suspected of containing said peptide;
   b) purifying said sample on a column of dextran cross-linked with epichlorohydrin;
   c) pooling the 50-20 kD molecular weight fractions, thereby forming a pooled sample;
   d) ethanol precipitating said pooled sample; and
   e) purifying said pooled sample on an Anti Ig column thereby producing a peptide of about 27 kD molecular weight.

* * * * *